United States Patent [19]

Palmer et al.

[11] Patent Number: 5,000,419
[45] Date of Patent: Mar. 19, 1991

[54] TUBE CLAMP

[75] Inventors: Davey B. Palmer, Highlands Ranch; Ferris J. Holmes, Louisville; Charles E. Elliott, Aurora, all of Colo.

[73] Assignee: Electromedics, Inc., Englewood, Colo.

[21] Appl. No.: 502,326

[22] Filed: Mar. 30, 1990

Related U.S. Application Data

[63] Continuation of Ser. No. 362,952, Jun. 7, 1989, abandoned.

[51] Int. Cl.$^5$ ............................................. F16K 7/04
[52] U.S. Cl. ............................................. 251/9; 251/4
[58] Field of Search ............................ 251/4, 7, 9

[56] References Cited

U.S. PATENT DOCUMENTS 3,942,228  3/1976  Buckman et al. ..................... 251/4

Primary Examiner—John C. Fox
Attorney, Agent, or Firm—Gary M. Polumbus

[57] ABSTRACT

A tube clamp for dependably occluding the flow of fluid through a deformable tube includes a pair of pin members mounted on a supporting surface adjacent to a pivotal body that includes an edge portion adapted to be pivoted into the space between the pin members to pinch the tube against the pin members, thereby occluding the flow of fluid through the tube.

3 Claims, 2 Drawing Sheets

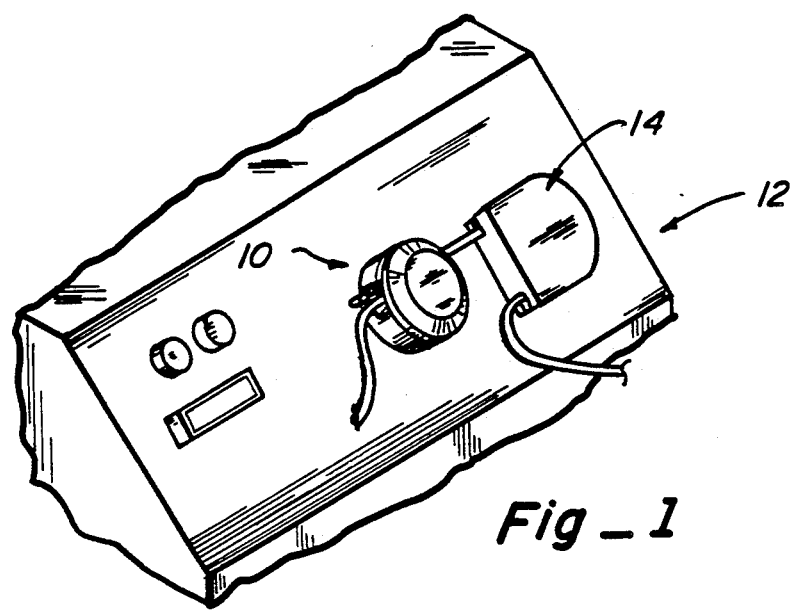
Fig_1
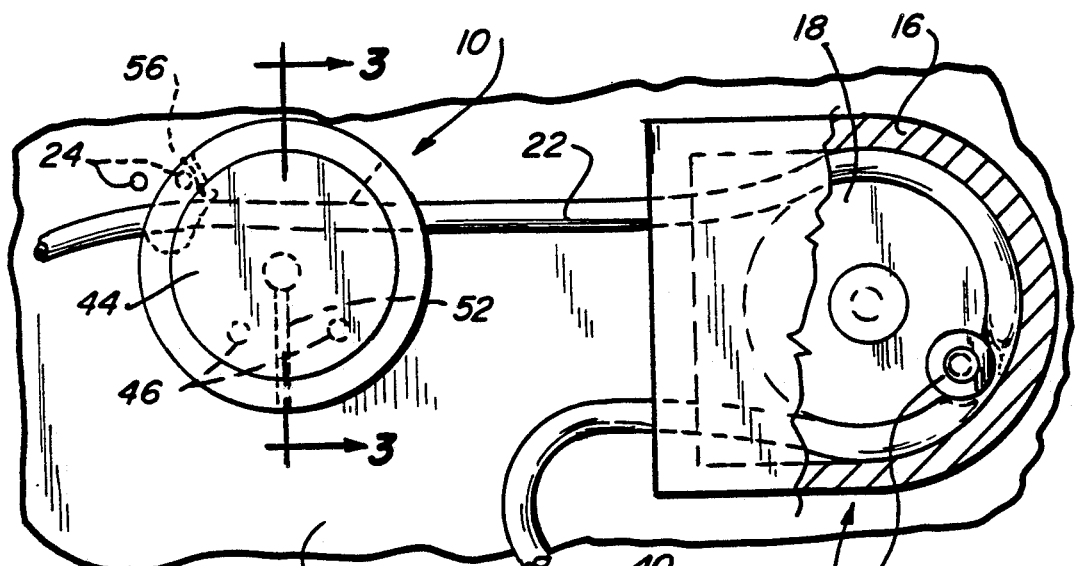
Fig_2
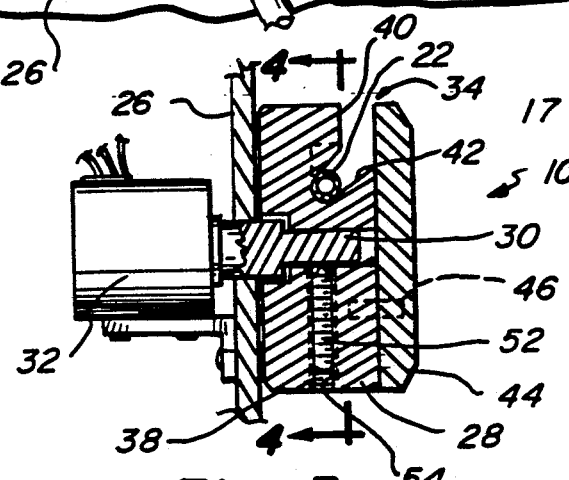
Fig_3

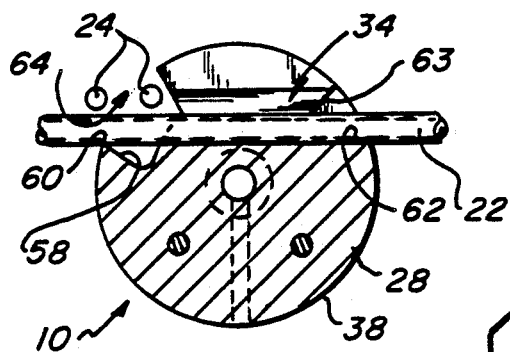
Fig_4
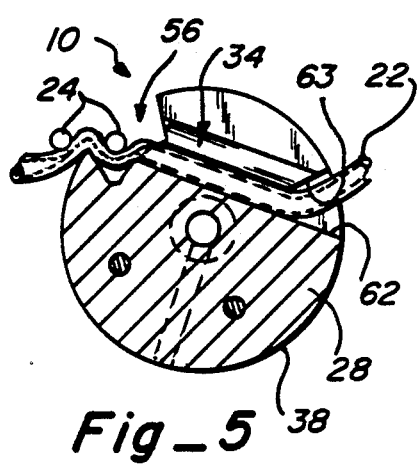
Fig_5
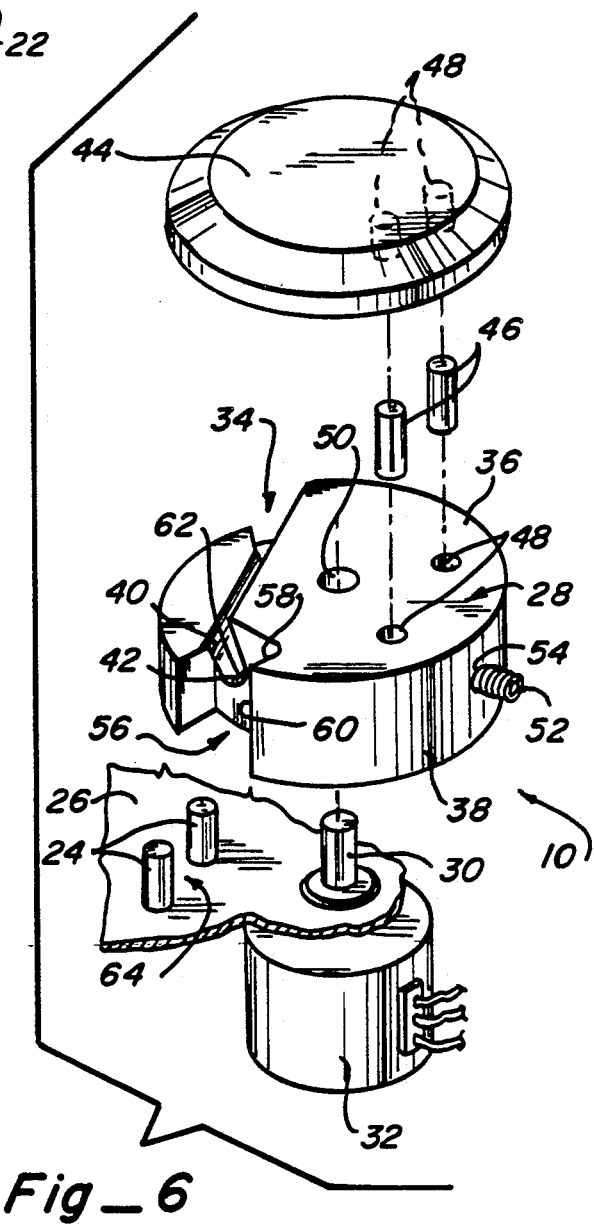
Fig_6

TUBE CLAMP

CROSS REFERENCE TO RELATED APPLICATIONS

This application is a continuation of application Ser. No. 07/362,952 filed June 7, 1989 for "Tube Clamp," now abandoned.

BACKGROUND OF THE INVENTION

1. Field of the Invention

The present invention relates generally to controlling the flow of fluid through a deformable tube and more particularly to a tube clamp adapted to selectively pinch the tube to thereby occlude the flow of fluid therethrough.

2. Description of the Prior Art

Numerous devices have been developed for occluding the flow of fluid through deformable tubes. Such devices have included cams for moving pinching arms against the tube to pinch the tube between the arms and a mandrel. Other devices utilize an eccentric to squeeze the tube against a mandrel to thereby occlude the flow of fluid therethrough, while still other devices utilize laterally moving rams such as may be activated by a solenoid to compress the tube against a mandrel to occlude the flow of fluid therethrough. There are numerous examples of such devices in the patented art of the United States.

Devices for occluding the flow of fluid through a deformable tube are used in the field of blood apheresis wherein a peristaltic pump is utilized to dispense citrate as an anticoagulant into a blood stream through a deformable tube. It is critical that the citrate be dispensed in precise quantities and, accordingly, a dependable system for satisfactorily occluding the flow of citrate through the tube is highly desirable.

In current apheresis equipment, the deformable tubes utilized in dispensing citrate are typically occluded by use of a solenoid actuated ram that pinches the tube against a mandrel disposed on the opposite side of the tube. Such devices have a number of drawbacks, however, in that they are loud when operated, the ram is preset to move a predesignated distance so that if the wall thickness of a deformable tube varies, the tube may not be fully occluded by the ram, the solenoids abruptly pinch the tube and therefore may cause damage thereto in prolonged usage and solenoids are known to have relatively high power consumption. In addition, solenoids generate more heat than is desired.

Accordingly, it would be desirable in apheresis systems to have a dependable mechanism for occluding the flow of citrate through a deformable tube which is quiet in operation, does not generate a lot of heat, has a relatively low power requirement, and occludes the flow of fluid through the tube in a manner such that the tube has a longer life. It is to satisfy these needs that the tube clamp of the present invention has been developed.

SUMMARY OF THE INVENTION

The tube clamp of the present invention is a quiet operating and gentle system for dependably occluding the flow of the fluid through a deformable tube. The tube clamp is ideally suited for use in apheresis systems for dispensing selected quantities of citrate in a dependable manner.

The tube clamp of the present invention includes a pair of spaced stationary contact surfaces on a supporting surface disposed adjacent to a pivotal member that is adapted to releasably retain a deformable tube in adjacent relationship to the contact surfaces. The pivotal member has an edge portion disposed adjacent to the contact surfaces on the opposite side of the deformable tube from the contact surfaces and is operable upon movement of the pivotal member to gently push the deformable tube into the space between the contact surfaces, thereby pinching the tube against each of the contact surfaces. The edge portion itself forces one side of the deformable tube against an opposite side thereby providing three locations of occlusion. In this manner, the flow of fluid through the tube is reliably prevented in a quiet and gentle manner so as to avoid the shortcomings of prior art systems.

Other aspects, features and details of the present invention can be more completely understood by reference to the following detailed description of a preferred embodiment, taken in conjunction with the drawings, and from the appended claims.

BRIEF DESCRIPTION OF THE DRAWINGS

FIG. 1 is a fragmentary perspective view of an apheresis machine including a peristaltic pump and the tube clamp of the present invention.

FIG. 2 is an enlarged fragmentary front elevation of the tube clamp of the present invention shown adjacent to a peristaltic pump with which it might be used.

FIG. 3 is a section taken along line 3—3 of FIG. 2.

FIG. 4 is a section taken along line 4—4 of FIG. 3.

FIG. 5 is a section similar to FIG. 4 with the tube clamp of the present invention in a pinching orientation.

FIG. 6 is an enlarged and exploded perspective view of the tube clamp of the present invention.

DESCRIPTION OF THE PREFERRED EMBODIMENT

The tube clamp 10 of the present invention finds an ideal use in administering predesignated dosages of chemicals in a medical application and by way of example the tube clamp is shown in FIG. 1 in an apheresis system 12 being disposed adjacent to a conventional peristaltic pump 14. The peristaltic pump, as probably best illustrated in FIG. 2, includes a curved mandrel 16 with a rotating disk 18 disposed in spaced but adjacent relationship to the inner surface of the curved mandrel. The rotating disk includes a system of rollers 20 disposed adjacent its peripheral edge that overlaps the peripheral edge of the rotating disk and is adapted to progressively deform and pinch a deformable tube 22 disposed in the space between the mandrel 16 and the disk 18 as the disk is rotated. It will, therefore, be appreciated that the system of rollers 20 serves to advance a charge of fluid, such as citrate, through the tube so that it can be directed toward the tube clamp 10 of the present invention. Peristaltic pumps are well known in the art and the particular pump described does not form a part of the present invention but is only described in illustrating a usage of the tube clamp of the present invention.

The tube clamp 10 of the invention is probably best illustrated in FIG. 6 as including a pair of cylindrical pin members or contact surfaces 24 mounted on a rigid supporting surface 26, and a pivotal body 28 mounted on the shaft 30 of an electric motor 32 which is also mounted on the support surface 26, with the motor being adapted to pivot the pivotal body 28 relative to the stationary pin members to occlude the flow of fluid through the deformable tube 22 in a manner to be described hereinafter.

The pivotal body 28 in the disclosed embodiment is illustrated as a cylindrical member having a slot 34 formed therein along a chord of the cylindrical body. The slot opens through an outer circular face 36 of the cylindrical body as well as along an arcuate segment of the cylindrical wall 38 of the body and includes a relatively narrow inner portion 40 that forms an acute angle with the pivotal axis of the cylindrical body and has tapered walls approximating the diameter of the tube to be clamped. The innermost end 42 of the slot has a width which is substantially equivalent to the outer diameter of the tube and thereby encourages the tube to remain in a specified position at the innermost extent of the slot without occluding the flow of fluid through the tube. A circular cap 44 is provided for attachment to the cylindrical body 28 over the circular face 36 thereof and overlies the portion of the slot which opens through the circular face. The cap 44, therefore, confines access to the inner portion 40 of the slot through the cylindrical wall 38 of the body so that the tube 22 can be inserted laterally into the slot and then angled inwardly to the innermost end 42 of the slot. The cap is retained in position in any suitable manner. In the disclosed embodiment, a pair of retention pins 46 are disposed and bonded in aligned recesses 48 provided in the cap and the circular face 36 of the cylindrical body. The cylindrical body further has a central axial passage 50 therethrough for receipt of the driven shaft 30 of the motor and a set screw 52 is threadedly received in a radial bore 54 of the cylindrical body to fix the cylindrical body to the shaft for unitary pivotal movement therewith.

A generally rectangular notch 56 is formed in the cylindrical wall 38 of the cylindrical body 28 in alignment with the slot 34 and defines a tapered surface 58 which cooperates with the cylindrical wall 38 to form a relatively sharp straight edge 60 along the cylindrical wall which is in alignment with the side 62 of the slot which is closest to the longitudinal axis of the cylindrical body. The relatively sharp edge 60 is, therefore, displaced from the slot 34 for a purpose which will become more clear later. The slot 34 has a flared wall 63 at the opposite end of the slot from the notch 56. The flared wall enlarges the entry to the slot so that the tube 22 is not pinched or occluded at this location when the cylindrical member is pivoted. This is best illustrated in FIG. 5.

The electric motor 32 is positioned on the supporting surface 26 so that in a beginning position as shown in FIG. 4, the relatively sharp edge 60 of the cylindrical body 28 is adjacent to and in alignment with the space 64 between the pin members. The relatively sharp edge is also spaced from the pin members so that the tube 22 to be clamped or occluded and which is disposed in the slot in the cylindrical body extends between the pin members 24 and the relatively sharp edge. The pin members lie on a line which is substantially parallel to the slot in the cylindrical body when the cylindrical body is in the beginning position of FIG. 4 so that the tube also extends parallel to the pins as it extends thereby.

As best shown in FIGS. 4 and 5, when the cylindrical body 28 is in the beginning position, the relative relationship of the pin members with the cylindrical body as mentioned previously are as illustrated in FIG. 4. Pivotal movement of the cylindrical body into the position shown in FIG. 5, however, causes the relatively sharp edge 60 of the cylindrical body to move into the space 64 between the pin members 24, thereby gently displacing the tube while squeezing it into the same space so that the walls of the tube are pinched against both of the pin members, thereby occluding the flow of fluid past the pin members. In addition, the edge 60 of the cylindrical body itself forces one side of the tube against an opposite side to provide a third location of occlusion, thereby establishing a very dependable and complete occlusion of fluid flow through the tube.

While the electric motor 32 could take different forms, in the preferred embodiment, it is a stepper motor which actually moves the cylindrical body in degreed increments but the movement is fast enough so that it appears to be a smooth movement. The stepping feature, however, permits adjustment of the system depending upon the wall thickness of the tube so that varying wall thicknesses can be accommodated and desirably pinched to occlude the flow of fluid therethrough.

Although the present invention has been described with a certain degree of particularity, it is understood that the present disclosure has been made by way of example, and changes in detail or structure may be made without departing from the spirit of the invention, as defined in the appended claims.

What is claimed is:

1. A system for pinching a deformable tube to occlude the flow of fluid therethrough comprising in combination, a pair of spaced stationary pin members mounted on a supporting surface, a generally cylindrical member mounted on said supporting surface adjacent to said pin members for pivotal movement about its longitudinal axis, said generally cylindrical member having a generally cylindrical wall spaced from said supporting surface, a slot formed in the generally cylindrical wall so as to extend along a chord of said generally cylindrical member, said slot being aligned with a path extending adjacent to said pin members and being adapted to releasably receive the tube to hold the tube in a position adjacent to said pin members, a notch formed in the generally cylindrical member in alignment with said slot and defining a generally sharp edge of the generally cylindrical member which is spaced from the slot and is adjacent to said pin members and on the opposite side of a tube received in the slot from the pin members, and motor means operatively connected to said generally cylindrical member for selectively pivoting the generally cylindrical member such that upon selected pivotal movement the generally sharp edge forces the tube into the space between the pin members causing the tube to be pinched against each pin member while the generally sharp edge forces one side of the tube against an opposite side of the tube to occlude the flow of fluid through the tube at three locations.

2. A system for pinching a deformable tube to occlude the flow of fluid therethrough comprising in combination, a pair of contact surfaces disposed in spaced relationship on a supporting surface, and a pivotal member mounted adjacent to said contact surfaces to cooperate with the contact surfaces in pinching said deformable tube, said pivotal member including a slot formed therein to releasably receive and retain said tube in a position adjacent to said contact surfaces, and a notch formed therein in alignment with said slot, said notch defining an edge portion on the pivotal member for forcing the tube into the space between the contact surfaces and into a deformed and pinched position between said edge portion and the contact surfaces upon selected pivotal movement of the pivotal member relative to the contact surfaces whereby the flow of fluid through the tube is occluded.

3. The system of claim 2 wherein said edge portion is spaced from said slot.

* * * * *